United States Patent [19]
Feldman et al.

[11] Patent Number: 5,131,845
[45] Date of Patent: Jul. 21, 1992

[54] LUBRICATING SYSTEM FOR A DENTAL HANDPIECE

[75] Inventors: Michael Feldman, Howell, N.J.; Moshe Meller, 175 Oberlin N. Ave., Lakewood, N.J. 08701

[73] Assignee: Moshe Meller, Princeton, N.J.

[21] Appl. No.: 697,312

[22] Filed: May 7, 1991

[51] Int. Cl.$^5$ .............. A61C 1/02; A61C 1/08; A61C 1/18; B43M 7/00
[52] U.S. Cl. ...................... 433/104; 206/63.5
[58] Field of Search .............. 433/104, 87, 89; 206/367, 368, 369, 634, 620; 221/197, 302

[56] References Cited

U.S. PATENT DOCUMENTS

| | | | |
|---|---|---|---|
| 1,680,616 | 8/1928 | Horst | 206/620 |
| 2,654,948 | 5/1950 | Rubin | 433/89 |
| 3,144,976 | 8/1964 | Freshour | 206/620 |
| 3,189,227 | 6/1965 | Hobbs | 206/620 |
| 3,331,499 | 7/1967 | Jost | 206/367 |
| 3,356,279 | 12/1967 | Root | 206/620 |
| 3,358,689 | 12/1967 | Higgins | 206/367 |
| 3,942,640 | 3/1976 | Hellstrom | 206/469 |
| 4,951,822 | 8/1990 | Fontana et al. | 206/530 |
| 5,009,894 | 4/1991 | Hsiao | 424/451 |
| 5,020,719 | 6/1991 | Roth et al. | 229/122.1 |

Primary Examiner—Gene Mancene
Assistant Examiner—Andy A. Cherichetti
Attorney, Agent, or Firm—Frishauf, Holtz, Goodman & Woodward

[57] ABSTRACT

A lubricant delivery system for a dental handpiece, the dental handpiece having an air inlet tube having a predetermined internal shape in the vicinity of an open end portion thereof. The lubricant delivery system comprises a squeezable sealed capsule which includes a main body portion and a necked down portion extending from the main body portion. The necked down portion is smaller than the internal shape of the air inlet tube and is insertable into the open end of the air inlet tube. A passage is formed in the necked down portion extending from the main body portion to a tip end portion of the necked down portion. A lubricant fills at least a part of the squeezable main body portion. When the tip end portion of the necked down portion is opened, the opened necked down portion is inserted into the air inlet tube of the dental handpiece and the main body portion is squeezed to expel lubricant contained therein into the handpiece via the air inlet tube. The capsule may be sealed within a packaging material, and may be packaged with or without an opening member, such as a sterile needle or the like. The air inlet tube may be designed to have an opening member, such as a needle, built therein, for piercing the tip end portion of the necked down portion of the capsule.

26 Claims, 2 Drawing Sheets

LUBRICATING SYSTEM FOR A DENTAL HANDPIECE

BACKGROUND OF THE INVENTION

This invention is directed to a lubricating system for a dental handpiece having moving parts and/or bearings which must be periodically lubricated for example, once or several times a day or before and after sterilization. The lubricating system must be clean in order to prevent the possible transmission of viral and bacterial matter to the patient and dentist or to otherwise contaminate the handpiece.

A dental handpiece is an elongated device which is normally held in or near a patient's mouth by the dentist when treating a patient. At the tip end of the handpiece, the dentist inserts various tools such as drills, polishing disks, cleaning tools, etc. At the base end of the handpiece are a series of tubes extending into the handpiece including at least an air inlet and a water inlet tube. The handpiece is separable from the main body of the dental unit to expose these tubes. When the handpiece is re-attached to the main body of the dental unit, these tubes match to corresponding tubes contained in a tubular member attached to the main body of the dental unit.

The dental handpiece itself includes moving parts and/or bearings which must be periodically lubricated to maintain efficiency and to prevent premature failure. Lubrication, depending on use, will usually be performed by the dentist or his staff once or twice (or more) a day, and before and after sterilization. Lubrication of the handpiece before and after sterilization is highly recommended.

PRIOR ART

The lubricating material is usually a light oil which is used to lubricate the moving parts and/or bearings in the handpiece, and which is safe for use in the mouth. Heretofore, the lubricating material is usually, for example, sprayed into the air inlet of the handpiece using an aerosol can. The dentist or technician in the office usually performs this procedure which required separating the handpiece from tubes leading to the main body of the unit to expose the air inlet tube of the handpiece and then spraying lubricating oil into the air inlet tube.

With the growing concern for health hazards resulting from retro viruses such as the AIDS virus and the Epstein-Barr virus, for example, it is possible that when the handpiece is lubricated with an aerosol can that the spray parts of the aerosol can itself may be contaminated by bacteria and viruses which are placed thereon when the dentist finds that he has to lubricate the handpiece and disconnects the handpiece in order to spray the lubricant into the air inlet.

At this point, the body and/or nozzle portion of the spray can may be contaminated by previous contact with a contaminated surface. Thus the dentist's hands will then be contaminated from holding the can. Alternately, the can may be contaminated by the dentist when he picks it up if his hands have been used to disconnect the handpiece from the main body of the dental unit without washing them first. As a result, when the dentist, after spraying the lubricant into the handpiece, re-connects the handpiece to the drilling unit, he can inadvertently contaminate the edges of the various tubes extending from the handpiece by inadvertent contact. When lubrication is again needed, the subsequent spraying may wash and blow the bacterial and viral matter from the tip edges of the tubes into the tubes themselves. If the spray can nozzle has been previously contaminated, then contaminated lubricant may be sprayed into the air inlet tube. This will then expose subsequent patients and the dentist to the bacterial and viral matter as air flowing into the air inlet tube is circulated in the vicinity of the handpiece. A similar contamination of the handpiece can arise when the dentist, who previously had gloves on, takes these gloves off and then touches the contaminated aerosol can which in turn contaminates his hands, or when the dentist puts on new gloves which he uses to pick up the can and the new gloves are then contaminated by the can. The dentist when reconnecting the handpiece can then inadvertently touch the tube ends with the contaminated gloves and the bacterial and viral matter on the tube ends can be washed and blown into the tubes during the subsequent lubricating spraying operation using an aerosol can. Then, when used in a patient's mouth, the bacterial and viral matter or other contamination could be blown into the patient's mouth by the compressed air.

Other sources of bacterial and viral matter exist in dental and medical offices. For example, the aerosol lubricating can may be lying in a drawer and a nurse or other clerical personnel or the dentist who had been in contact with a patient or with contaminated instruments used during the dental process, or with patient's saliva, can inadvertently touch the can and may contaminate the outside thereof when the can is subsequently picked up for lubricating the handpiece. The contaminants on the can may can be inadvertently transferred to the edges of the tube and then subsequently washed or blown into the tubes themselves which in turn can present a hazard to both the dentist and the patients being treated by the dentist.

OBJECTS AND SUMMARY OF THE INVENTION

It is therefore an object of the present invention to provide a safe, inexpensive, disposable lubricating delivery method and system and package for a dental handpiece having moving parts therein which must be lubricated periodically to maintain efficiency.

The dental handpiece has an air inlet tube which includes an end portion, said air inlet tube being used to receive lubricant to lubricate the moving parts in the handpiece and to compressed air to the handpiece. The end of the air inlet tube is contaminable by bacterial and viral matter by unintended contact with non-sterile surfaces.

According to the present invention, a lubricant delivery system comprises a squeezable sealed capsule having a main body with a necked down portion which is smaller than the air inlet tube and which can be inserted into the air inlet tube; the necked down portion of the capsule having a tip end portion; a passage extending from the main capsule body to the tip end portion; and means for opening the passage at the tip end portion to permit lubricant to flow out of the capsule into the dental air inlet tube after the passage has been opened and said capsule has been inserted into the air inlet tube.

It is another object of the present invention to provide a method for lubricating a dental handpiece having moving parts therein which have to be lubricated to maintain efficiency and prevent damage, said handpiece having an air inlet tube having an end portion with a predetermined opening, said end portion being contaminable by bacterial and viral matter inadvertently coming in contact therewith. The method of the present invention comprises providing the air inlet tube at the open end portion thereof with an opening which has a predetermined shape; encapsulating a lubricating material in a squeezable capsule; providing said capsule with a necked down portion with at least a tip end portion of said necked down portion being smaller than said predetermined shape of the opening of the air inlet tube to enable the necked down portion of the capsule to be inserted a predetermined distance into the air inlet tube; providing a passage in the necked down portion which extends to the tip end portion thereof to provide a flow path for the lubricant to flow out of the capsule when the passage is opened at the tip end portion of the necked down portion; opening the passage at the tip end portion of the necked down portion when the moving parts in the handpiece are to be lubricated; then inserting the tip end of the opened necked down portion a predetermined distance into the air inlet tube after the passage has been opened; and squeezing the capsule to expel lubricant therein into the air inlet tube.

It is another object of the present invention to provide a sealed packaged unit for use in lubricating a dental handpiece which comprises a combination of a squeezable capsule lubricant delivery system according to the present invention sealed in a packaging material to maintain the cleanliness of the lubricating delivery system until it is required to be used.

It is a further object of the invention to provide a dental handpiece lubricating system which comprises a large number of squeezable capsule lubricant delivery devices described above, contained within a dispensing-type box so that the user can remove one capsule at a time from the dispensing box, to maintain cleanliness of the squeezable capsule lubricant delivery devices

DETAILED DESCRIPTION

Figure 1:
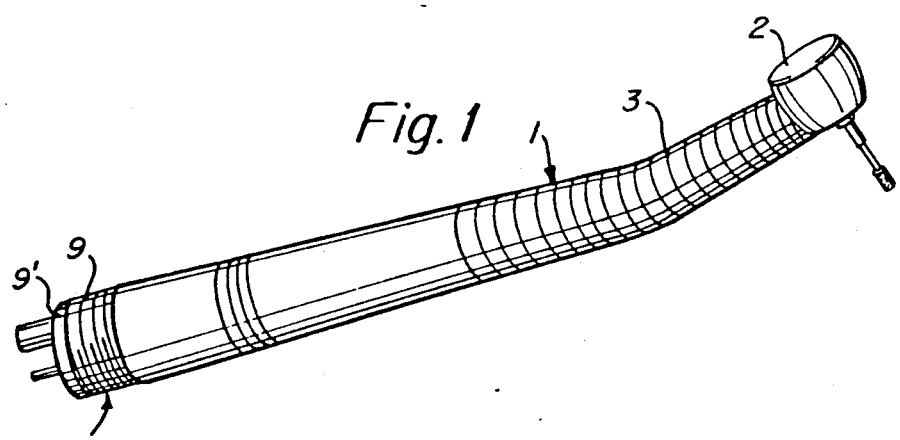
FIG. 1 is a perspective view of a handpiece which is to be lubricated in accordance with the present invention.

FIG. 1 shows a typical example of a dental handpiece 1 which is generally used by the dental profession in the United States and throughout the world. The dental handpiece with which the lubricating system of the present invention is useable can be any of the types of handpieces generally known in the art. For example, the handpiece may be straight, angular, slow speed or high speed. The motion imparted at the working end of the handpiece can be rotational (for example, a drill) or vibrational (for example, in a scaler or other cleaning device). The air connection to the handpiece may be the standard four hole or three hole system, or can be a two hole or any other connecting system which has at least one air inlet tube through which the lubricant can be applied. The description given herein is for a dental drill having a four hole or four tube connection system as shown in FIG. 1A. The description is given only by way of example, and it should be clear that various other types of handpieces could be used with the lubricant delivery system of the present invention, as will be apparent from the following.

Figure 2:
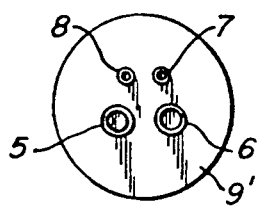
FIG. 2 is an end view of the proximal end of the handpiece showing in detail the air inlet and outlet tubes and water inlet

Typically, the handpiece 1 has an end portion 2 to which are attached various tools used by the dentist such as drills, sanding or grinding discs, cleaning discs, etc. Moving parts in the handpiece then transmit the required motion to the tools attached to working end 2. A holding portion generally shown at 3 is held by the dentist when he is using the handpiece. The handpiece is attached to the tubes leading to the main body of the dental unit which provides compressed air, water, etc. to the handpiece upon attachment of the proximal end designated at 26 (see also FIGS. 2 and 3) which includes tubes emanating from the proximal end which mate with corresponding tubes in an elongated drive tube connected to the main body of the dental unit. The tubes at the proximal end 26 include air inlet tube 5, air outlet tube 6, blowing air inlet tube 7 and another tube 8. These tubes are usually mounted through a threaded end portion 9 having a resilient gasket or disc member 9' fixed at the end of the handpiece 1. The end portion 26 will threadably mate with a connecting device (not shown) of the tubular unit connected to the main body of the dental unit which will connect at least a controllable source of air to the air inlet and a source of water to the water inlet tubes. Connections other than screw threads for connecting to the drive tube of the dental unit could be used. FIG. 2 is an end view of the proximal end of the dental handpiece illustrated in FIG. 1. The end portion 9 through which the tubes 6–8 are mounted can be a cylindrical member made of hard plastic material (autoclavable) or other suitable material. Gasket 9' is made of silicon rubber or other resilient plastic material.

Figure 3:
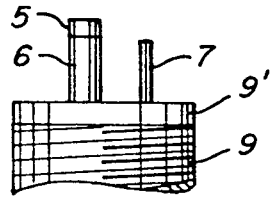
FIG. 3 is a side view of the proximal end of the handpiece.

FIG. 3 is a side view of the proximal end of the handpiece shown in FIG. 1. The proximal end has been rotated so that the tube 6 is in front of the tube 5 which normally extends somewhat beyond tube 6 measured from the end portion 9. Tube 7 blocks the view of tube 8 which is aligned with tube 7. The end portion 9 has the tubes mounted therethrough to communicate with the interior of the main body of the handpiece, as is conventional. The main body of the handpiece includes moving parts therein such as bearings which are used to convert the energy supplied from the main body of the dental unit to turn or move the tools mounted at the working end portion 2.

As noted previously, periodically the bearings and other internal mechanisms (not shown) in the main body and working end portion (head) of the handpiece (not shown) have to be lubricated in order to keep the efficiency of the handpiece within the desired range to prolong the life of the unit, and to prevent premature failure. Also, the handpiece should be lubricated both before and after sterilization thereof. In order to lubricate the moving parts in the interior of the main body of the handpiece, the proximal end 26 thereof must be disconnected from the tubes leading to the main body of the dental unit and lubricant from a lubricating aerosol can is normally sprayed into the air inlet tube 5 and the handpiece is then reconnected to the main body of the drilling unit. In view of the possible presence of bacteria or viral matter on the exposed top edge or end portion of tube 5 which has become more prevalent as a result of retro viruses such as the AIDS virus and the Epstein-Barr virus, concern for cleanliness of all medical environments has grown tremendously in order to insure the safety and health of the patients, as well as the dentist or other personnel operating the unit. As the fear of infection rises, due to the prevalence of the retro viruses discussed immediately above, sterilization between patients is becoming more highly desirable and is becoming recommended procedure. Thus, the dental handpieces should be sterilized more often than in the past, and this means that lubrication must be applied more often than in the past. As mentioned hereinabove, it is highly recommended, for best operation of the handpiece, that the handpiece be lubricated both before and after sterilization. This will result in more handling of the handpiece, and more possibility of contamination by virtue of application of contaminated lubricant, lubricant applicators, hands, or the like. Thus, when practicing between patient sterilization of the handpiece, the present invention becomes even more important.

When the dentist determines that the handpiece has to be lubricated, possibly after treating a patient, or before and after sterlization, the handpiece is disconnected from the connecting device and then lubricant is sprayed in the air inlet tube 5. If this procedure is used, whatever bacterial matter is on the dentist's hands at the time he picks up the aerosol can, will possibly transfer onto the can itself. If the tube 5 is contaminated, the contamination may be transferred to the spray nozzle portion of the aerosol can. Also, the can is in a dental office where other viruses and bacteria, perhaps not as dangerous as the retro viruses, can also be placed inadvertently on the can by other personnel working in the office such as nurses or clerks who may be rummaging through a drawer in which the can is present. When the dentist subsequently picks up the aerosol can and then sprays it into the air inlet the spraying may dislodge viral and bacterial matter on the nozzle and/or the surfaces of the tubes 5, 6, 7 and 8 and may blow and wash that material into the tubes within the main body of the handpiece. Alternately, the dentist, while trying to reconnect the handpiece to the main body of the drilling unit, may inadvertently touch the ends of the tubes 5, 6, 7 and 8 with gloves with which he just treated his patients and it is possible that bacterial and viral matter from the patient or the aerosol can might then lodge on the exposed ends of the tubes 5, 6, 7 and 8. This material will then subsequently be blown into or flow into the tubes by use of the aerosol spray, thus potentially contaminating the interior of the tubes. Also, the nozzle of the spray can may pick up contamination at this time and contaminate the next item to be lubricated.

The foregoing creates a particularly dangerous condition when a high speed turbine-type handpiece is used. In such a device, the handpiece sprays air and water and carries the contaminated lubricant and other viruses and/or bacterial matter directly into the mouth of the patient, thereby increasing the risk of infection to the patient. Still further, as mentioned above, between-patient sterilization is becoming a more highly recommended procedure for reducing the risk of cross-infection. However, the use of the same lubricant can or container over and over again, is a contradiction to the theory of between-patient sterilization, since the previously used lubricant container can re-contaminate an already sterile handpiece which was immediately previously sterilized.

Figure 4:
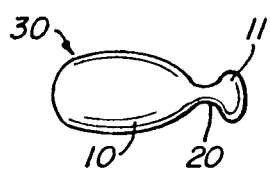
FIG. 4 shows a first embodiment of the lubricant delivery system of the present invention.

In order to overcome the problems discussed above, FIG. 4 shows a first embodiment of the lubricant delivery system of the present invention. Referring to FIG. 4, the lubricating delivery system 30 of the present invention comprises a biodegradable, flexible and squeezable hollow shell 10 which has a hollow main body portion 10, a necked down portion 20 extending from the main body portion 10, and a winged or enlarged end portion 11. A liquid lubricant is filled in the main body portion 10 of the shell and the necked down portion 20 is formed so that the winged portion 11 can be twisted off manually or with a tool to open a lubricant delivery passage 12 as shown in FIGS. 4A and 5.

Figure 4A:
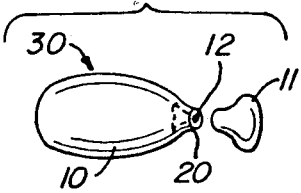
FIG. 4A shows the delivery system shown in FIG. 4 in its separated condition.
Figure 5:
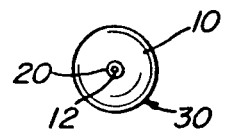
FIG. 5 is an end view of capsule 10 of FIG. 4A.

FIG. 4A shows the winged portion 11 twisted off from the main body portion 10 shown in FIG. 4, leaving open the lubricant delivery passage opening 12 which communicates with the interior of main body portion 10. Shell 30 can be made of a gelatin type material (to be described later) or of a flexible PVC (or other flexible material) material which preferably will biodegrade. Non-biodegradable materials can be used, but biodegradable materials are preferred for shell 30. The lubricant delivery system 30 shown in FIG. 4 is intended to be a single-use device which is totally disposable. That is, after the lubricant has been squeezed into the air intake tube 5, the shell 10 and the wing portion 11 are thrown away with other refuse in the dental office. The term "single use" includes lubricating a single handpiece or a plurality of handpieces together, for example after sterilization. A single capsule generally contains sufficient lubricant for several handpieces. It is disposed of after such "single use".

In operation, after the necked down portion 20 has been opened (to expose passage 12) by twisting off the winged portion 11 from the main shell portion 10, the remaining necked down (reduced-size) portion 20 with the lubricant delivery opening or passage 12 therein is inserted into the air inlet tube 5 shown in FIGS. 1 and 2 and squeezed. This squeezes the lubricant into the interior of the main body 1 of the handpiece and will lubricate the moving parts and bearings therein to maintain the efficiency of that unit.

The necked down portion 20 of the unit 30 shown in FIG. 4 is designed to just fit into the air inlet valve 5 so that the point at which the lubricant is inserted into the air inlet is below the top edge surface of the tube 5 and thus any material, bacterial or viral, which is on the top or free edge surface of the air inlet tube 5 will not be blown or washed into the air tube 5. The open and used lubricant shell 10 (and wing portion 11) is disposed of with other refuse.

The thickness of the material of shell 10 is approximately 0.2 millimeters in a presently preferred embodiment wherein the shell 10 is made of a biodegradable gelatin. Other thicknesses could be used as will be described hereinbelow. Shell 10 is filled (or partly filled) with an extremely light, dental grade, FDA approved lubricating oil which is required for the handpiece 10 and which is widely used in the art.

Figure 6:
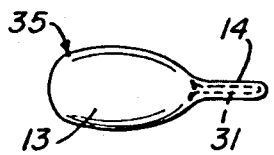
FIG. 6 shows a second embodiment of the lubricant delivery system of the present invention.
Figure 6A:
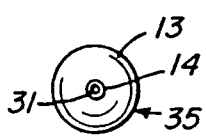
FIG. 6A is an end view of FIG. 6.

Another embodiment of the lubricant delivery system of the present invention is shown in FIG. 6, wherein a lubricant delivery system 35 includes a shell 13 made of a gelatin like material or a PVC (or other plastic) squeezable type material which encapsulates therein a very light oil (as described above) for use in lubricating the handpiece shown in FIG. 1. The lubricant delivery system in FIG. 6 has a necked down sealed end portion 14 extending from the main body portion 13. The necked down end portion 14 has a channel 31 therein which communicates with the interior of body portion 13. The necked down end portion 14 is designed to fit into the air inlet tube 5 shown in FIG. 1. In order to open the channel 31 so that the lubricant can escape through the internal passage 31 in necked down end portion 14, a sterile scissor or other cutting implement can be used to snip off or pierce the distal end of the necked down end portion 14. After the end portion of tube 14 has been snipped off, the top or end view of the device 35 with the end thereof snipped off is as shown in FIG. 6A with the opening 31 therein. The neck 14 of shell 13 with the end portion snipped off is then inserted into the air inlet tube 5 in handpiece 1 and squeezed so that the lubricant is provided to the moving parts in the handpiece, as required to maintain its efficiency.

Figure 7:
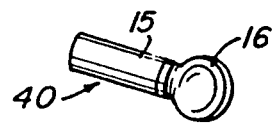
FIG. 7 shows a sterile needle device which may be used with the lubricant delivery systems of FIGS. 4 and 6.
Figure 8:
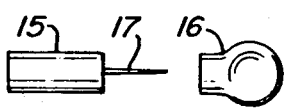
FIG. 8 shows the device in FIG. 7 when it is separated.

Since it is sometimes difficult to maintain the cleanliness of a scissor, clipper or other cutting implement in a dental office because it will contact the dentist's or other practitioner's hands, the present invention envisions that the lubricant delivery system should include its own sterile device which will always remain sterile regardless of conditions within the dental office. Such a device is shown generally at 40 in FIGS. 7 and 8. The device of FIGS. 7 and 8 has a sterile needle device 17 housed in a base portion 15 and an end portion 16 is mounted over the needle. The separated portions 15 and 16 of FIG. 7 are shown in FIG. 8 with needle 17 shown exposed in FIG. 8 after the portions 15 and 16 have been separated from each other. After the needle holding portion 15 is separated from the covering portion 16, the exposed needle is used to open the channel or passage at the end of the necked down portion 14 shown in FIG. 6. This will insure that the tip end portion 14 of capsule is pierced by a sterile needle which will not contaminate the end thereof. The device 40 shown in FIG. 7 can also be used with the lubricant delivery system shown in FIG. 4 in which the twisted off portion of the delivery system 3 therein will have a clean exposed end surface and the needle can then be inserted into the clean exposed end surface to insure that the passage 12 is open. The needle 17 is required or may be required if the opening of passage 12 of FIG. 4A for some reason is sealed off because the winged portion 11 when twisted does not open the opening, or if the channel 12 was not properly formed within the shell 10. Alternately, unit 30 of FIG. 4 can be designed so that the twist off portion 11 intentionally does not open the channel and the needle 17 will be required to open said channel.

Figure 9:
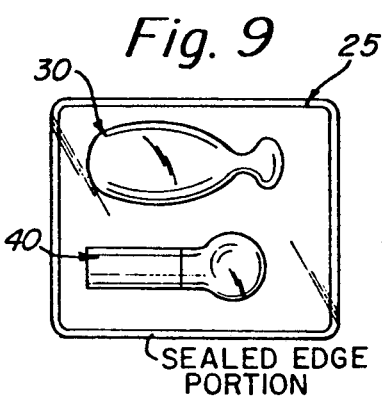
FIG. 9 shows a packaging arrangement including the device of the delivery system of FIG. 4 and the sterile needle shown in FIG. 7.
Figure 10:
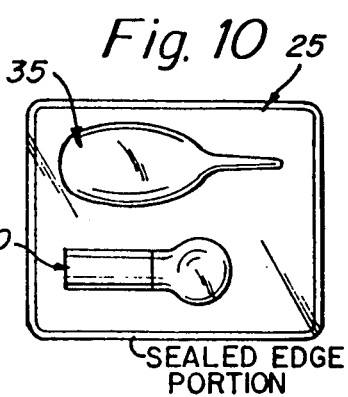
FIG. 10 shows a packaging arrangement for the device shown in FIG. 6 and the sterile needle shown in FIG. 7.

It is remotely possible that the shells 30 in FIG. 4 and the shells 35 shown in FIG. 6, if left in a box or other unattended or open container within the dental office, can become contaminated by bacterial and viral matter as a result of handling by the dental professionals and the nurses and clerical staff. In order to overcome this potential problem, and to more positively insure the cleanliness of the lubricating delivery system, the present invention also provides a package 25 shown in FIG. 9 which includes the unit 30 shown in FIG. 4 in combination with the unit 40 shown in FIG. 7. Alternately, the packaging 25 as shown in FIG. 10 can contain a combination of the lubrication delivery unit 35 shown in FIG. 6 and the piercing means 40 shown in FIG. 7. Still further, the package 25 may contain only a lubrication shell unit 30, 35, sealed therein, without a piercing needle unit 40. The package 25 can be made of material which can be opened easily and thrown away and also should preferably be made of biodegradable material. Materials may be thin plastic film, cellophane, or other thin plastic materials that can be heat sealed or otherwise sealed around their edges, and which can thereafter be easily opened.

Figure 11:
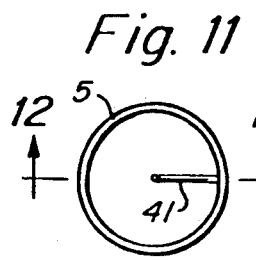
FIG. 11 shows an enlarged top view of a modified air inlet tube of the present invention in which a piercing needle 41 is mounted in the air inlet tube at a distance below the top edge surface of the tube.
Figure 12:
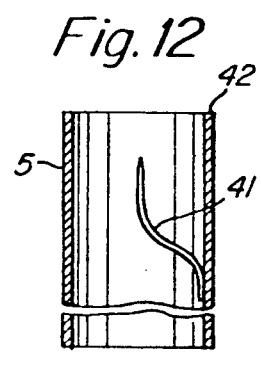
FIG. 12 is a sectional view of FIG. 11 and shows needle 41 mounted on the side wall of tube 5 at a distance below the top edge so that it will pierce the capsule neck portion 1 shown in FIG. 6, or the neck portion of FIG. 4 after the winged portion 1 has been twisted off as shown in FIG. 4A.

FIG. 12 is a cross-section view of part of air inlet tube 5 with a needle 41 mounted therein at a distance below the top edge 42, which distance is less than the length of the neck portions 20, 14 of the capsules shown in FIGS. 4 and 6, respectively. FIG. 11 is a top view thereof. In this configuration, when necked down portion 14 of the capsule 14 shown in FIG. 6 is inserted into tube 5, the needle 41 will pierce the end thereof and the capsule is backed off of the needle to allow lubricant to flow out of the passage 12 of the squeezed capsule when the capsule is slightly lifted off the needle after piercing thereof.

Figure 13:
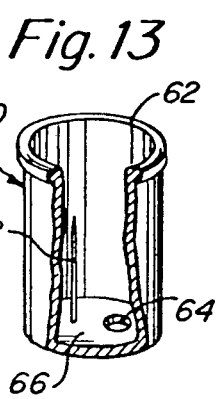
FIG. 13 is an enlarged perspective, partially cut away view of a cylindrical reducer for being inserted in the air inlet tube 5 and which includes a piercing mechanism therein.
Figure 14:
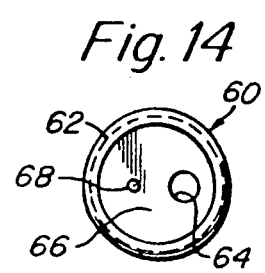
FIG. 14 is a top view of the reducer of FIG. 13.

FIGS. 13 and 14 show a reducer sleeve which is adapted to be inserted into the open end of the air inlet tube 5. The inlet sleeve 60 has an outer diameter which snugly fits within the air inlet tube 5. The open end of the reducer 60 has a ridge or enlarged rim portion 62 to prevent the reducer sleeve 60 from being inserted too far into the air inlet tube 5. The outer diameter of the enlarged ridge or rim 62 is slightly larger than the inner diameter of the air inlet tube 5 to act as a "stop member" for the reducer 60. The reducer 60 has an off-center opening 64 therein for permitting air to flow into the air inlet tube 5. In many instances, it is necessary to reduce the amount of air flow for proper operation of the handpiece or for other reasons associated with the dental treatment. The bottom surface 66 of the reducer member 60 is a substantially solid wall having a needle 68 extending therefrom in an upward direction. The needle 68 has a sharp tip which is designed to pierce the necked down portion 14, 20 or the like of a capsule 30, 35. After piercing by pressing on the needle 68, the capsule is backed off and squeezed to expel lubricant from the capsule so that the lubricant passes into the opening 64 to lubricate the internal portions of the dental handpiece. The sleeve 60 can be made of metallic material (preferred), but could also be made of plastic or other suitably strong material. When the reducing member 60 is made of metallic material, the needle or pin 68 is preferably welded, brazed or the like to the bottom surface 66 thereof.

Figure 15:
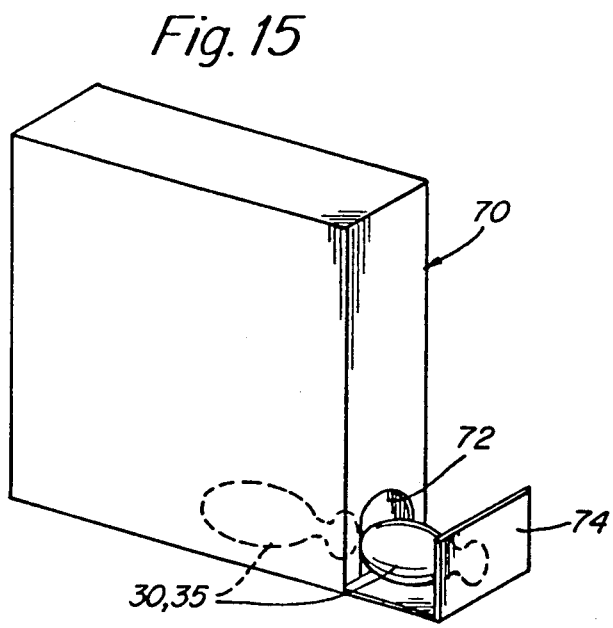
FIG. 15 is a perspective view of a dispensing box containing a large number of capsules of the present invention.

FIG. 15 is a perspective view of a dispensing box 70 containing a large number of capsules 30, 35 or the like therein, which can be dispensed one-by-one at a dispensing outlet 72. The box preferably contains a large number of capsules (for example, 100 or 144, etc.) which are "loose" in the box 70. An adhesively secured covering portion 74 covers the opening portion 72. When desired to be used, the adhesive portion 74 is pulled back to expose the opening 72, and the box is either shaken to dispense the capsules 30, 35 one-at-a-time, or the practitioner may pull out the capsules one at a time, for example with a finger, tweezers, pliers or the like. The vertical portion 74 serves as a "stop" for contacting a dispensed capsule (see FIG. 15) to prevent a plurality of capsules from being dispensed at one time. Other dispensing containers could be used, the one shown in FIG. 15 being shown only by way of example.

As mentioned hereinabove, a preferred thickness for the capsule 30, 35, when made of gelatin material, is about 0.2 mm, with a tolerance of about + or − of 0.1 mm. The thickness is not critical, but the capsule, depending on the materials used, should be sufficiently flexible so as to permit squeezing thereof to expel lubricant therein, after the end portion is opened by piercing, cutting, twisting off, or the like. A typical thickness range could be, for example, 0.05 mm to 0.5 mm, depending upon the softness or flexibility of the material used. The preferred material at present is gelatin, since it is biodegradable. However, other materials, such as PVC or other plastics, nylon materials, or the like could be used.

In a typical non-limiting example, the overall length of the capsule 30 shown in FIG. 4 (including the wing 11) is about 2.5 cm, with the main body portion 10 of the shell being about 1 ¾ cm. Typically, the shell may have a diameter of about 1 cm. The diameter of the shells are not critical; they could be as small as about ½ cm or greater than 1 cm, so long as the necked down portion is sufficiently small to be inserted into the air tube 5. In a typical example, the following materials are used:
 oil type: very light white mineral oil;
 ingredients of shell (approximate weight percentages):
  gelatin—63%;
  glycerin, USP 96%—35%
  timica silc white—1.2%
  plus trace amounts (less than about 0.07% each of titanium dioxide, USP; FD & C red #40; external D & C Violet #2; D & C red #33).

The above example is given only by way of example, it being clear that wide variations in the constituent elements of the shell material, the dimensions of the shell and the type of oil may be used, as desired.

As seen from the foregoing, the present invention is directed to a system which helps to insure the public that the dental maintenance functions for the handpiece 1 shown in FIG. 1 will not be a source of bacterial or viral infection to the patients and/or dental personnel.

It is obvious that modifications can be made to the lubricant delivery system, method and packaging of the present invention, within the scope of the present invention as defined by the appended claims.

We claim:

1. A clean dental lubricant delivery system for a dental handpiece having moving parts therein which must be lubricated periodically to maintain the efficiency thereof, said dental handpiece having an air inlet tube having a predetermined internal shape in the vicinity of an open end portion thereof, said open end portion being contaminable by bacteria and viral matter by unintended contact therewith,
 said dental lubricant delivery system comprising a plurality of separate, unconnected, squeezable sealed capsules housed in a sealed closed container and removable one-by-one from said sealed closed container after opening of said container, each said capsule including:
 a main body portion and a necked down portion extending from said body portion;
 said necked down portion being smaller than said predetermined internal shape of said air inlet tube and being insertable into said open end of said air inlet tube;
 said necked down portion having a tip end portion;
 a passage formed in said necked down portion, said passage extending from said body portion to said tip end portion;
 a dental lubricant filling at least a part of said body portion of said capsule; and
 means for opening said passage at said tip end portion of said capsule to permit said dental lubricant to flow out of said body portion of said capsule, via said necked down portion, and into said air inlet tube of said dental handpiece after said passage has been opened and said necked down portion of said capsule has been inserted into said open end portion of said air inlet tube.

2. The lubricant delivery system of claim 1, wherein said means for opening said passage comprises an enlarged portion formed at the tip end portion said necked down portion, said enlarged portion being separable from said necked down portion to open said channel upon twisting of said enlarged portion relative to said capsule.

3. The lubricant delivery system of claim 1, wherein said means for opening said passage comprises piercing means.

4. The lubricant delivery system of claim 3, wherein said piercing means comprises a holder; a sterile needle mounted on said holder and a sheathing mounted over said needle for maintaining the sterility of said needle; said sheathing being removable by twisting relative to said holder to separate said sheathing from said holder to expose said sterile needle.

5. The lubricant delivery system of claim 3, wherein said piercing means comprises a needle mounted in said air inlet tube to pierce said necked down portion of said capsule as said necked down portion of said capsule is inserted into said air inlet tube, said needle being mounted to be entirely below said open end portion of said air inlet tube.

6. The lubricant delivery system of claim 1, wherein said capsule is formed of a gelatin which is degradable after said lubricant has been squeezed out.

7. The lubricant delivery system of claim 6, wherein said gelatin material is about 0.2 mm thick.

8. The lubricant delivery system of claim 1, wherein said capsule is formed of a PVC material.

9. The lubricant delivery system of claim 7, wherein said PVC material is about 0.2 mm thick.

10. The lubricant delivery system of claim 1 wherein said means for opening said passage comprises cutting means for cutting off said tip portion of said capsule.

11. The lubricant delivery system of claim 1, wherein said container includes dispensing means for dispensing said plurality of capsules one at a time therefrom.

12. The lubricant delivery system of claim 11, wherein said dispensing means includes an opening at a lower end of said container through which said capsules are dispensed one at a time.

13. The lubricant delivery system according to claim 11, wherein said dispensing means further comprises a stop member adjacent said opening and spaced from said opening for contacting a dispensed capsule, and for preventing a plurality of dispensed capsules from being dispensed at the same time.

14. A method for lubricating a dental handpiece having moving parts therein which have to be lubricated periodically to maintain efficiency and prevent damage, said handpiece having an air inlet tube having a predetermined internal shape in the vicinity of an open end portion thereof, said open end portion being contaminable by bacteria and viral matter by unintended contact therewith, comprising:
  encapsulating a lubricating material in at least a main body portion of a squeezable capsule;
  providing said capsule with a necked down portion having a tip end portion, said necked down portion extending from said body portion and being configured to fit into said predetermined shape of said open end portion of said air inlet tube to enable said necked down portion of said capsule to be inserted into said open end of said air inlet tube;
  providing a passage in said necked down portion which extends to said tip end portion of said necked down portion capsule to provide a passage for said lubricant to flow out of said body portion of said capsule when said passage is opened at said tip end portion;
  opening said passage at said tip end portion of said necked down portion, when said moving parts in said handpiece are to be lubricated;
  inserting said opened necked down portion into said open end portion of said air inlet tube; and then
  squeezing said capsule to expel said lubricant therein into said air inlet tube to lubricate said moving parts of said handpiece.

15. The method according to claim 14, wherein said opening step comprises cutting off a tip end portion of said necked down portion to open said passage.

16. The method according to claim 14, wherein said opening step comprises piercing said tip end portion of said necked down portion with a sharp object.

17. The method according to claim 16 further comprising providing a needle for piercing said tip end portion of said capsule and enclosing said needle and said capsule in a sealed envelope.

18. The method according to claim 14 further comprising: positioning a needle in said air inlet tube such that upon insertion of said necked down portion of said capsule into said tube, said needle will pierce said tip end portion of said necked down portion to open said passage.

19. The method according to claim 14, further comprising the step of enclosing said capsule in a sealed envelope.

20. The method according to claim 14, wherein said opening step comprises breaking off a tip end portion of said necked down portion to open said passage.

21. The method according to claim 14, comprising providing a container containing a plurality of said capsules packaged in said container, said container being sealed after receiving said plurality of capsules therein; and removing said capsules one-by-one from said container.

22. A method for lubricating a dental handpiece having moving parts therein which have to be lubricated periodically to maintain efficiency and prevent damage, said handpiece having an air inlet tube having a predetermined internal shape in the vicinity of an open end portion thereof, said open end portion being contaminable by bacteria and viral matter by unintended contact therewith, comprising:
  encapsulating a lubricating material in a squeezable capsule;
  providing said capsule with a necked down portion having a tip end portion which is smaller than said predetermined shape of said open end portion of said air inlet tube to enable said necked down portion of said capsule to be inserted into said air inlet tube;
  providing a fluid passage in said necked down portion which extends to said tip end portion of said necked down portion to provide a flow path for said lubricant to flow out of said capsule when said passage is opened at said tip end portion of said necked down portion;
  providing a tip end breakaway portion at said tip end portion of said necked down portion which, upon twisting relative to the remainder of said capsule, will break away from said necked down portion to open said passage;
  breaking away said tip end breakaway portion from said capsule when said handpiece is to be lubricated; then
  inserting said opened necked down portion into said open end portion of said air inlet tube; and then
  squeezing said capsule to expel lubricant therein into said air inlet tube.

23. The method of claim 22, further comprising positioning a needle in said air inlet tube which upon insertion of said necked down portion of said capsule into said open end portion of said tube will pierce said tip end portion of said necked down portion to open said passage.

24. The method of claim 22, further comprising packaging said capsule in a sealed package.

25. A method for lubricating a dental handpiece having moving parts therein which have to be lubricated periodically to maintain efficiency and prevent damage, said handpiece having an air inlet tube having a predetermined internal shape in the vicinity of an open end portion thereof, said open end portion being contaminable by bacteria and viral matter by unintended contact therewith, and in which a lubricating material is encapsulated in at least a main body portion of a squeezable capsule; the capsule including a necked down portion having a tip end portion, said necked down portion extending from said body portion and being configured to fit into said predetermined shape of said open end portion of said air inlet tube to enable said necked down portion of said capsule to be inserted into said open end of said air inlet tube; said necked down portion being provided with a passage which extends to said tip end portion of said necked down portion to provide a passage for said lubricant to flow out of said body portion of said capsule when said passage is opened at said tip end portion;

the method comprising:

opening said passage at said tip end portion of said necked down portion, when said moving parts in said handpiece are to be lubricated; then inserting said opened necked down portion into said open end portion of said air inlet tube; and then squeezing said capsule to expel said lubricant therein into said air inlet tube to lubricate said moving parts of said handpiece.

26. A clean dental lubricant delivery system for a dental handpiece having moving parts therein which must be lubricated periodically to maintain the efficiency thereof, said dental handpiece having an air inlet tube having a predetermined internal shape in the vicinity of an open end portion thereof, said open end portion being contaminable by bacteria and viral matter by unintended contact therewith, said dental lubricant delivery system comprising a squeezable sealed capsule including:

a main body portion and a necked down portion extending from said body portion;

said necked down portion being smaller than said predetermined internal shape of said air inlet tube and being insertable into said open end of said air inlet tube;

said necked down portion having a tip end portion;

a passage formed in said necked down portion, said passage extending from said body portion to said tip end portion;

a dental lubricant filling at least a part of said body portion of said capsule; and means for opening said passage at said tip end portion of said capsule to permit said dental lubricant to flow out of said body portion of said capsule, via said necked down portion, and into said air inlet tube of said dental handpiece after said passage has been opened and said necked down portion of said capsule has been inserted into said open end portion of said air inlet tube; and wherein said means for opening said passage comprises piercing means, and said piercing means comprising a piercing member mounted in said air inlet tube to pierce said necked down portion of said capsule as said necked down portion of said capsule is inserted into said air inlet tube, said piercing member being mounted to be entirely below said open end portion of said air inlet tube.

* * * * *